United States Patent [19]

Sauer et al.

[11] Patent Number: 5,547,958
[45] Date of Patent: Aug. 20, 1996

[54] N-(8α-ERGOLINYL)-AMIDES

[75] Inventors: Gerhard Sauer; Thomas Brumby; Helmut Wachtel; Jonathan Turner; Peter-Andreas Löschmann, all of Berlin, Germany

[73] Assignee: Schering Aktiengesellschaft, Berlin, Germany

[21] Appl. No.: 364,015

[22] Filed: Dec. 27, 1994

Related U.S. Application Data

[63] Continuation of Ser. No. 79,833, Jun. 21, 1993, abandoned, which is a continuation of Ser. No. 872,390, Apr. 23, 1992, abandoned, which is a division of Ser. No. 522,751, May 14, 1990, Pat. No. 5,212,178.

[30] Foreign Application Priority Data

May 12, 1989 [DE] Germany ............... 39 15 950.7

[51] Int. Cl.⁶ ............... A61K 31/48; A61K 31/44; C07D 457/12; C07D 457/02
[52] U.S. Cl. ............... 514/288; 546/18; 546/68
[58] Field of Search ............... 546/18, 68; 514/288

[56] References Cited

U.S. PATENT DOCUMENTS

| | | | |
|---|---|---|---|
| 2,864,822 | 12/1958 | Fornefeld et al. | 546/68 |
| 4,764,517 | 8/1988 | Gull | 546/68 X |
| 4,766,128 | 8/1988 | Sauer et al. | 546/68 X |
| 4,772,610 | 9/1988 | Biere et al. | 546/68 X |
| 4,791,115 | 12/1988 | Habfliger | 546/68 X |
| 4,826,852 | 5/1989 | Haffer et al. | 546/68 X |
| 4,950,672 | 8/1992 | Habfliger | 514/288 |

FOREIGN PATENT DOCUMENTS

| | | | |
|---|---|---|---|
| 1175813 | 10/1984 | Canada | 546/68 |
| 0160842 | 11/1985 | European Pat. Off. | 546/68 |
| 0250357 | 12/1987 | European Pat. Off. | 546/68 |
| 3500251 | 7/1985 | Germany | 546/68 |
| 615929 | 6/1975 | Switzerland | 546/68 |
| 2135307 | 8/1984 | United Kingdom | 546/68 |
| 2185743 | 7/1987 | United Kingdom | 546/68 |

OTHER PUBLICATIONS

Nordmann et al, Helvetica Chem. Acta, vol. 69, pp. 246 to 250 (1986).

Stutz et al, Eur. J. Med Chem.-Chim.Ther, vol. 17, pp. 537–541 (1982).

Primary Examiner—Floyd D. Higel
Attorney, Agent, or Firm—Millen, White, Zelano & Branigan, P.C.

[57] ABSTRACT

8α-acylamino ergolines are useful dopamine agonists.

17 Claims, No Drawings

N-(8α-ERGOLINYL)-AMIDES

This application is a continuation of Ser. No. 08/079,883, filed Jun. 21, 1993 (abandoned); which is a continuation of Ser. No. 07/872,390, filed Apr. 23, 1990 (abandoned); which is a division of Ser. No. 07/522,751, filed May 14, 1990 (now U.S. Pat. No. 5,212,178); the disclosures of which are hereby incorporated by reference.

BACKGROUND OF THE INVENTION

The invention relates to 8α-acylaminoergolines, their production and use as pharmaceutical agents, and intermediate compounds for the production of 8α-acylaminoergolines.

8α-acylaminoergolines described in DOS35 00 251 show prolactin secretion inhibitory effect. If long-chain alkyl radicals are present in the 6-position, they especially inhibit the secretion of the luteinizing hormone. 8α-diethyl-urea and thiourea ergoline derivatives, which have a long-chain hydrocarbon radical in the 6-position, are described in EP-A-351 352. The 8α-acylaminoergoline derivatives substituted in the 6-position with a long-chain hydrocarbon radical show, in comparison with the 6-methyl derivatives, a reduced apomorphine antagonistic activity and increased dopamine agonistic activity. At the same time, the metabolic stability of the compound is maintained or improved.

SUMMARY OF THE INVENTION

The invention relates to compounds of Formula I

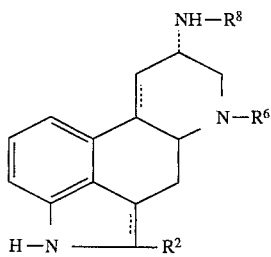

in which

C....C each independently is a single or double bond, $R^2$ is optionally substituted $C_{1-7}$ alkyl, $C_{2-7}$ alkenyl, $CH_2$—O—$C_{1-4}$ alkyl or $CH_2$—S—C—$_{1-4}$ alkyl, $R^6$ is $C_{2-6}$ alkyl, $C_{3-6}$ alkenyl or $C_{3-5}$ cycloalkyl-$C_{1-2}$ alkyl and $R^8$ is —$CXR^3$ or —$SO_2R^5$, in which $R^3$ is hydrogen, optionally substituted $C_{1-6}$ alkyl, S—$C_{1-6}$ alkyl, —O—$(CH_2)_n$—$N(CH_3)_2$ or $NR^9R^{10}$, X is oxygen or sulfur and means $R^5$ $CH_3$ or an amino group optionally monosubstituted or disubstituted with $C_{1-4}$ alkyl, in which $R^9$ and $R^{10}$ is each independently hydrogen, $C_{1-4}$ alkyl, $C_{3-4}$ alkenyl, —$(CH_2)_n N(CH_3)_2$, $CH_2CF_3$ or together with the nitrogen atom form a 5–6 member, saturated or unsaturated heterocycle, which can be interrupted by one to two other heteroatoms, and n=1,2,3 or 4 as well as their acid addition salts and $C_2$ ....$C_3$ is a single bond, if $R^2$ is methyl and $R^8$ is CO—$C_{1-6}$ alkyl and $R^8$ does not mean CXN $(C_2H_5)_2$.

All alkyl groups can be straight-chain or branched alkyl radicals, for example, methyl, ethyl, n-propyl isopropyl, n-butyl, isobutyl, sec-butyl, tert-butyl, pentyl, hexyl , heptyl, 2,2-dimethylpropyl, 2-methylbutyl, 3-methylbutyl, 1-ethyl-buryl, isopentyl, isoleptyl, 1-methyl-1-ethylpropyl, and the like Alkyl radicals $R^2$ can be substituted, especially in the 1-position, with 1–3 of hydroxy, $C_{1-4}$-alkoxy, $C_{2-5}$-acyloxy (e.g., alkanoyloxy), or a group corresponding to the formula —C(OR')R"R"', in which R" and R'" each independently mean hydrogen or alkyl radicals with a maximum of 6 carbon atoms and R' especially is hydrogen or acetyl or an S—$C_{1-4}$-alkyl group. Suitable acyl groups are derived from aliphatic carboxylic acids such as, for example, acetic acid, propionic acid, butyric acid, caproic acid, and trimethylacetic acid.

If $R^2$ or $R^6$ mean an alkenyl radical, the latter preferably contains only one double bond, and the double bond in radical $R^6$ cannot be adjacent to the nitrogen atom. Suitable as alkenyl radicals, for example, are: vinyl, 1-propenyl, 2-propenyl, 1-methyl- 2-propenyl, 1-butenyl, methallyl, allyl, etc.

If $R^6$ means a cycloalkyl-alkyl group, for example, cyclopropylmethyl, cyclopropylethyl, cyclobutylethyl, cyclopentylmethyl, cyclopentylethyl are included.

Alkyl radical $R^3$ can be singly or doubly substituted with hydroxy, $C_{1-4}$ alkoxy, acetyloxy or dimethylamino groups, and alkyl groups with up to 3 carbon atoms and a substituent are preferred. If $R^9$ and $R^{10}$, together with the nitrogen atom form a saturated or unsaturated heterocycle, the latter can be interrupted by oxygen, sulfur or an NH group optionally substituted with alkyl or phenyl, or can contain 2 nitrogen atoms. For example, morpholine, thiomorpholine, piperidine, imidazolidine, piperazine, pyrrolidine, pyrazolidine, imidazole, triazole, etc., are suitable.

$C_{2-4}$ alkyl, $C_{3-4}$ alkenyl or cycloalkylalkyl with up to 5 carbon atoms can be considered as suitable embodiment forms for $R^6$ and $C_{1-4}$ alkyls and $C_{2-4}$ alkenyls for $R^2$.

The compounds of Formula I can occur as E or Z isomers or, if a chiral center is present in radical $R^2$, as diastereomers and as their mixtures. Both the individual isomers per se and the isomer mixtures are included in this invention. The physiologically compatible acid addition salts can be derived from known inorganic and organic acids, such as, for example, hydrochloric acid, sulfuric acid, hydrobromic acid, citric acid, maleic acid, fumaric acid, tartaric acid, etc.

The compounds of Formula I, as well as their acid addition salts, especially exhibit central dopaminergic effectiveness and, therefore, can be used as pharmaceutical agents. Since they are especially distinguished by dopamine agonistic action, without α-adrenergic effects being noticeable, the compounds according to the invention are especially suitable for treatment of dopamine deficiency conditions in living beings (e.g., mammals, including humans) and especially of Parkinson's Disease.

For use of the compounds according to the invention as pharmaceutical agents, they can be produced in the form of a pharmaceutical preparation which, besides the active ingredient, contain pharmaceutical, organic, or inorganic inert vehicles, such as, for example, water, gelatin, gum arabic, lactose, starch, magnesium stearate, talc, vegetable oils, polyalkylene glycols, etc., suitable for enteral or parenteral application. The pharmaceutical preparations can be present in solid form, for example, as tablets, dragees, suppositories, capsules, or in liquid form, for example, as solutions, suspensions, or emulsions. Optionally, they further contain auxiliary agents such as preservatives, stabilizing agents, wetting agents, or emulsifiers, salts for changing the osmotic pressure, or buffers.

All compounds of this invention for treatment of Parkinson's Disease can be administered by any conventional route, e.g., parenterally or orally. A suitable dosage range is 0.00001–0.1 mg/kg/day, especially 0.001–0.1 mg/kg/day.

Typically, unit dosages are 0.001–10 mg/dosage unit in a physiologically acceptable carrier. In general, they can be administered analogously to the administration of the known agent bromocryptine. Particular levels of activity and, correspondingly, more precise details of administration can be routinely determined for any given compound in conjunction with a standard pharmaceutical test such as that of Horowski et al., below.

The dopamine agonistic action was determined according to Horowski, R. and Wachtel, H. Eur. J. Pharmaz. col. 36: 373–383, 1976. One hour after i.p. pretreatment with test substance or vehicle, the presence of behavior stereotypes on rats (masticatory, licking, or gnawing movements) was determined for 2 minutes (60th–62nd min. p.i.). Animals which during the 2-minute interval showed masticatory, licking, or gnawing movements were considered as stereotypes.

The results are presented in Table 1.

TABLE 1

Stereotype-releasing effectiveness on rats 1 hour after i.p. pretreatment. Effective doses ($ED_{50}$) with 95% confidence limit were determined with the help of probit analysis, n = number of animals:

| Compound | n | $ED_{50}$ | Effectiveness 95% Confidence Limit |
|---|---|---|---|
| A | 8 | 0.080 | 0.010–0.170 |
| B | 8 | 0.050 | 0.034–0.079 |

A = N-(2-methyl-6-n-propyl-8α-ergolinyl)-dithiocarbamic acid methyl ester
B = N-(2-methyl-6-n-propyl-8α-ergolinyl)-thioformamide The production of the compounds according to the invention of Formula I can be performed according to methods known in the art.

For example, the compounds of formula 1 can be attained by a) a compound of formula II

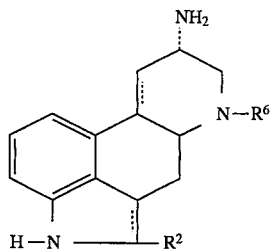

in which $R^2$ and $R^6$ have the above meaning, being acylated with an acid or its functional derivative, b) a compound of formula II and a compound of formula III $$R^9-N=C=X \quad \text{III}$$

in which $R^9$ and X have the above meaning, but $R^9$ cannot be hydrogen, being reacted to form a compound with $R^8$ meaning $-CX-NHR^9$, c) a compound of formula IV

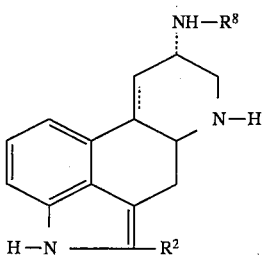

in which $R^2$ and $R^8$ have the above meaning, being alkylated or alkenylated d) a compound of formula V

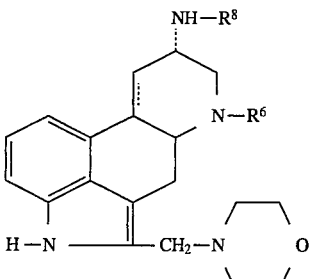

in which $R^6$ and $R^8$ have the above meaning, being substituted in the 2 position e) a compound of formula VI

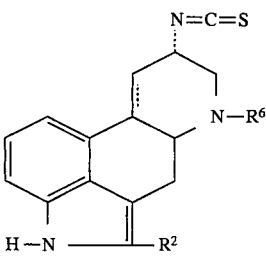

in which $R^2$ and $R^6$ have the above-named meaning, being converted with a nucleophile to compounds of formula I with $R^3=-S-C_{1-6}$ alkyl, $-O-(CH_2)_n-N(CH_3)_2$ or $NR^9R^{10}$ in which $R^9$, $R^{10}$ and n have the above-named meaning and optionally then a C—C single bond being oxidized or a C—C double bond being reduced or a carbonyl group being thiolated or forming the acid addition salts.

The acylation of the compounds of formula I according to process a) can be performed in the usual way. Thus, free acid $R^8OH$ or its reactive derivatives such as halides or anhydrides can be reacted with the amine of formula II optionally in the presence of a base in a suitable inert solvent at temperatures from room temperature to the boiling temperature of the solution mixture. Suitable as solvents are ethers such as tetrahydrofuran, dioxane, chlorinated hydrocarbons such as dichloromethane or aprotic solvents such as DMF. In the use of an anhydride for acylation, also excess anhydride can be used as solvent. The formulation is suitably performed with a mixed anhydride of acetic acid and formic acid. Suitable as bases are, for example, triethylamine, Huenig bases or 2,6-lutidine or the acylation is performed in pyridine as solvent. The production of urea and thiourea derivatives can take place, for example, by reactive imidazolides, which are obtained from N,N-carbonyldiimidazole or N,N-thiocarbonyldiimidfzole and primary and secondary amines $R^9R^{10}HN$. Also urea derivatives; can be also prepared by reaction with carbamoylchlorides $R^9R^{10}NCO$ Cl.

The addition of amines on isocyanates or isothiocyanates according to process b) can take place according to the method described in EP-82 808, by the reaction being performed, for example, in an inert solvent such as hydrocarbons, chlorinated hydrocarbons, ethers or esters, for example, in hexane, toluene, dichloromethane, diethyl ether, ethyl acetate, etc. at room temperature or elevated temperature.

The introduction of substituents in the 6 or 2 position can take place before or after the acylation in the 8 position.

Substitution in the 6 position according to process c) can be performed, for example, according to A. Cerny et al. Coll. Czech. Comm. 49, 2828 (1984) or according to the process described in EP-21 206, by the 6H compound of formula IV being reacted with the corresponding $R^6$ halides (bromides, chlorides, iodides). The reaction suitably takes place in an inert solvent such as dimethyl sulfoxide, dimethylformamide, acetonitrile or nitromethane in the presence of bases such as alkali hydroxides or carbonates.

The introduction of substituents $R^2$ can take place, for example, according to the processes described in EP-A-351 352. Here the Mannich base of formula V or its quaternary salt can be nucleophilically substituted or introduced by the 2-aldehyde derivative as intermediate compound of desired substituent $R^2$. The nucleophilic exchange takes place optionally after quaternizaton of the Mannich base in a polar, protic or aprotic solvent such as alcohols, ethers or chlorinated hydrocarbons at room temperature or elevated temperature, and alcoholates or thiolates can be used as nucleophilic anions, which optionally can then be converted into the $CH_2$ OH group. For the production of the 2-methyl derivative, the quaternary salt of formula V in polar solvents such as alcohols can be reduced with sodium borohydride.

The oxidation to a 2—CHO compound can take place analogously to the process described in R. A. Jones and al. Synthetic Communications 16, 1799 (1986) with manganese dioxide or tertbutyl hypochlorite in inert solvents at room temperature. The conversion of the 2-formyl compounds to compounds of formula I, in which $R^2$ means an alkenyl radical, can take place in a Wittig reaction, as, for example, with alkyl triphenylphosphonium halide in polar solvents such as cyclic and acyclic ethers, chlorinated hydrocarbons, dimethylformamide or dimethyl sulfoxide at temperatures of −50° C. to the boiling temperature of the reaction mixture, and strong bases such as alkali alcoholates, lithium organyl, etc., are added for the production of the ylene.

The preparation of substituents $R^2$ hydroxylated in the 1 position can take place, for example, by reaction of aldehydes and ketones with Grignard compounds or lithium organyls. The Grignardization can take place with the usual Grignard reagents such as alkyl magnesium halides in an aprotic solvent such as cyclic and acyclic ethers at low temperatures (−70° C. to 0° C.). The reaction with alkyl lithium takes place under analogous conditions.

The acylation of a hydroxyl group can take place according to the usual methods such as by reaction with acid anhydrides or acid chlorides.

If substituent $R^2$ contains a hydroxyl group, the latter, for example, can reduced by reaction with Na $BH_4$ in glacial acetic acid to the corresponding 2-alkyl derivative or oxidized with magnesium dioxide to the ketone or dehydrated with the introduction of a double bond. If substituent $R^2$ contains a double bond, the latter, for example, can be catalytically reduced. The introduction of substituent $R^2$ —C(OH)R"R''' can take place, as described above, by the reaction of the ketone with Grignard compounds or lithium organyls.

If the compounds of formula I are prepared according to process e), the reaction conditions mentioned under process variant b) are suitable for the reaction. Alcohols, primary and secondary amines and mercaptans of formula H-$R^3$ can be used as nucleophiles, and $R^3$ means —S—$C_{1-6}$ alkyl, —O—$(CH_2)_n$—$N(CH_3)_2$ or $NR^9 R^{10}$.

The optionally subsequent stereoselective hydrogenation of the 2,3-double bond can take place, for example, according to the process described in EP-A-286 575 in the presence of an acid with organylsilanes or with hydrogen/noble metal catalysts.

If optionally the introduction of the $C_2$–$C_3$ double bond is to be performed, the latter can take place, for example, according to the process described in EP-A-190534 with tert-butyl hypochlorite or with $MnO_2$ according to EP-A-118849.

The conversion of the amides and urea derivatives into the thioamides and thiourea derivatives can take place, for example, according to the process described in EP-A-217 730 by reaction with phosphorus oxychloride and a thiolation agent or with Lawesson reagent according to Fieser and Fieser Reagents for Org. Synth. IX, 49. The compounds of formula I are isolated either as free bases or in the form of their physiologically compatible acid addition salts.

For the formation of salts a compound of formula I, for example, is dissolved in a little methanol or methylene chloride and mixed with a concentrated solution of the desired acid.

The isomer mixtures can be separated according to the usual methods, such as, for example, crystallization, chromatography or salt formation in the diastereomers or E/Z isomers.

The invention also comprises compounds of formula II

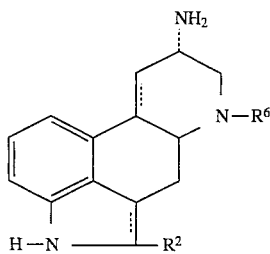

in which $R^2$ and $R^6$ have the above meaning and the compounds of formula IV

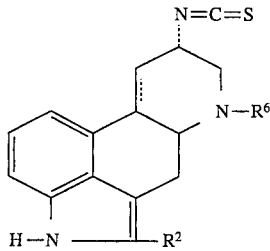

in which $R^2$ and $R^6$ have the above meaning.

These compounds are valuable intermediate products for the production of pharmacologically effective compounds. The conversion of the intermediate products into the active ingredients takes place according to the above-described processes.

If the production of the initial compounds is not described herein, they are known or can be produced analogously to known compounds or processes described here using known or readily preparable starting materials.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above and below, and of corresponding West German Application No. P39 15 950.7, filed May 12, 1989, are hereby incorporated by reference.

Starting Compounds

Preparation of 2,6-disubstituted 8alpha-amino-ergolines

1) A solution of 25 mmol of lithium diisopropylamide in 50 ml of tetrahydrofuran is prepared and the solution of 3.38 g of 6-n-propyl-2-vinyl-8beta-ergoline carboxylic acid methyl ester (10 mmol) in 50 ml of tetrahydrofuran is added at −30° C., it is stirred for 30 minutes at this temperature and then acidified with 10% hydrochloric acid. After heating to room temperature it is mixed with saturated bicarbonate solution, shaken out with dichloromethane and the organic phase is separated, dried and concentrated by evaporation. The residue is chromatographed on silica gel with dichloromethane/methanol. Yield of 6-n-propyl- 2-vinyl-8alpha-ergoline carboxylic acid methyl ester 2.0 g (60% of theory).

Without crystallization, the 8 alpha-ester is converted with hydrazine hydrate/hydrazine hydrochloride in propanol into the corresponding hydrazine, nitrosated with sodium nitrite in hydrochloric acid solution to 8 alpha-ergoline carboxylic acid azide and the azide is rearranged at 80° C. After cooling, it is worked up as described above and the residue is crystallized. Yield 3 g (45% of theory) of 6-n-propyl-2-vinyl-8alpha-ergolinyl-amine.

Other substituted ergolinyl, amines can be prepared analogously.

2) 4.35 g of 1,1-diethyl-3-(2-methyl-6-n-propyl-8alpha-ergolinyl) urea (11 mmol) is suspended in 1N HCl and heated for hours to 120° C. The solution is permitted to cool, carefully made alkaline with ammonia solution and extracted with dichloromethane. The residue is crystallized from dichloromethane/methanol/diisopropyl ether. Yield 2.69 g (83% of theory) of 2-methyl-6-n-propyl-8alpha-ergolinyl-amine, $[\alpha]_D=-82°$. (0.5% in chloroform)

Analogously, the following ergolinylamines are prepared from the corresponding ergolinyl ureas or ergolinyl thioureas:
6-ethyl-2-methyl-8alpha-ergolinylamine yield 74%
6-allyl-2-methyl-8alpha-ergolinylamine yield 53%
6-cyclopropylmethyl-2-methyl-8alpha-ergolinylamine yield 59%
2,6-diethyl-8alpha-ergolinylamine yield 76%
2-ethyl-6-n-propyl-8alpha-ergolinylamine yield 81%
2-ethyl -6-allyl-8alpha-ergolinylamine yield 71%
(6-ethyl-2-morphilinomethy-8alpha-ergolinylamine yield 71%
2-morpholinomethyl-6-n-propyl-8alpha-ergolinylamine yield 80%

3) 880 mg of 3-(9,10-didehydro-2-methyl-6-n-propyl-8alpha-ergolinyl)- 1,1-diethylurea (2.3mmol) is dissolved in 30 ml of trifluoroacetic acid and 1.48 ml of triethylsilane is added in three equal portions at intervals of 5 minutes. Then it is stirred for 60 minutes, first ice then 25% ammonia solution with cooling are added and the alkaline solution is shaken out with dichloromethane. The organic phases are dried and concentrated by evaporation. Yield after chromatography 378 mg. By crystallization from ethyl acetate/diisopropyl ether, 106 mg of the 2,3-dihydro derivative can be obtained, $[\alpha]_D=+204°$ (0.5% in chloroform).

271 mg of the crude product is heated in 40 ml of 4 N HCl for 16 hours to 110° C. After cooling, it is mixed with ice, made alkaline with ammonia and shaken out from dichloromethane. The crude product is crystallized from ethyl acetate/diisopropyl ether. Yield 46 mg (23% of theory) of 9,10-didehydro-2,3beta-dihydro- 2beta-methyl-6-n-propyl-8alpha-ergolinylamine, $[\alpha]_D=+81°$ C. (0.2% in chloroform).

Analogously, the following 9,10-didehydro-2,3beta-dihydro- 8alpha-ergolinylamines are prepared from the corresponding 9,10-didehydro-ergolinyl ureas:

9,10-didehydro-2,3beta-dihydro-6-ethyl-2beta-methyl-8alpha-ergolinylamine yield 31%

6-allyl-9,10-didehydro-2,3beta-dihydro-2beta-methyl-8alpha-ergolinylamine yield 19%

6-cyclopropylmethyl-9,10-didehydro-2,3-dihydro-2beta-methyl-8alpha-ergolinylamine yield 32%

9,10-didehydro-2,3beta-dihydro-2,6-diethyl-8alpha-ergolinylamine yield 41%

9,10-didehydro-2,3-didehydro-2-ethyl-6-n-propyl-8alpha-ergolinylamine yield 35%

6-allyl-9,10-didehydro-2,3-beta-dihydro-2-ethyl-8alpha-ergolinylamine yield 49%

2,3-dihydro-8alpha-ergolinylamine can be prepared from the corresponding ergolinyl ureas according to the same specifications.

2,3beta-dihydro-2-methyl-6-n-propyl-8alpha-ergolinylamine yield 65%

2,3beta-didehydro-6-ethyl-2-methyl-8-alpha-ergolinylamine yield 73%

6-allyl-2,3beta-dihydro-2-methyl-8alpha-ergolinylamine yield 63%

2,3-dihydro-2-ethyl-6-n-propyl-8-alpha-ergolinylamine yield 78%

EXAMPLE 1

(Dimethylamino)-(2-methyl-6-n-propyl-8alpha-ergolinylamino)-sulfone 30 ml of dichloromethane,-10 ml of 2,6-lutidine and 1 ml of dimethylaminosulfonic acid chloride (10 mmol) are mixed at room temperature. The suspension of 300 mg of 2-methyl-6-n-propyl-8alpha-ergolinylamine (1.06 mmol) in 30 ml of dichloromethane is added to it and stirred for 16 hours at room temperature and then 2 hours at 50° C. The reaction solution is shaken three times with 200 ml each of saturated copper sulfate solution, the organic phase is washed with water, dried and concentrated by evaporation, finally in a high vacuum. The crude product is chromatographed on silica gel with dichloromethane/methanol and crystallized from ethyl acetate/diisopropyl ether/hexane. Yield 73 mg (17% of theory), $[\alpha]_D=-44.9°$ (0.5% of chloroform).

Analogously, there is produced with diethylaminosulfonic acid chloride: (diethylamino)-(2-methyl-6-n-propyl-8alpha-ergolinylamino)-sulfone. Yield 25% as tartaric acid salt, $[\alpha]_D=-34°$ (0.5% in methanol).

EXAMPLE 2

Analogously to example 1, there is prepared from 9,10-didehydro- 2,3beta-dihydro-2-methyl-6-n-propyl-8-alpha-ergolinylamine:

(9,10-didehydro-2,3beta-dihydro-2-methyl-6-n-8alpha-ergolinylamino)-dimethylaminosulfone, yield 37%.

EXAMPLE 3

(9,10-didehydre-2-methyl-6-n-propyl-8alpha-ergolinyl)-dimethylamino-sulfone 390 mg of (9,10-didehydro2,3beta-dihydro-2-methyl-6-n-propyl- 8alpha-ergolinylamino)-dimethylamino-sulfon (1 mmol) is dissolved in 30 ml of anhydrous tetrahydrofuran and 0.5 ml of triethylamine and the mixture is cooled to −40° C. 0.16 ml of tert-butyl hypochlorite (1.34 mmol) in 10 of anhydrous tetrahydrofuran is instilled and stirred for 30 minutes at −40° C. The mixture is poured onto ice, made alkaline with ammonia and extracted with dichloromethane. The organic phases are dried, concentrated by evaporation and the residue is chromatographed on silica gel with dichloromethane/methanol and crystallized. Yield 217 mg (56% of theory).

EXAMPLE 4

N-(2-methyl-6-n-propyl-8alpha-ergolinyl)-formamide 849 mg of 2-methyl-6-n-propyl-8alpha-ergolinylamine (3 mmol) is dissolved in 40 ml of tetrahydrofuran and 3.75 ml of a mixture of 6.15 ml of 98% formic acid, 12.5 ml of acetic anhydride and 10 ml of anhydrous tetrahydrofuran are added. After 30 minutes of stirring at room temperature, ice is added, it is made alkaline with ammonia and shaken out with dichloromethane. The organic phases is dried, the solvent is evaporated and the residue is chromatographed on silica gel with ethyl acetate/methanol and crystallized from diisopropyl ether, yield 647 mg (69% of theory), $[\alpha]_D=+30°$, (0.5% in chloroform).

Analogously there are prepared:
- from 2,3beta-dihydro-2-methyl-6-n-propyl-8alpha-ergolinylamine the N-2,3beta-dihydro-2-methyl-6-n-propyl-8alpha-ergolinyl)-formamide, yield 61%
- from 2-ethyl-6-n-propyl-8alpha-ergolinylamine the N-(2-ethyl- 6-n-propyl-8alpha-ergolinyl)-formamide, yield 63%
- from 9,10-didehydro-2,3beta-dihydro-2-methyl-6-n-propyl- 8alpha-ergolinylamine the N-(9,10-didehydro-2,3beta-dihydro-2-methyl- 6-n-propyl-8alpha-ergolinyl)-formamide, yield 73%
- from 6-allyl-9,10-didehydro-2,3beta-dihydro-2-methyl-8-alpha-ergolinylamine the N-(6-allyl-9,10-didehydro-2,3beta-dihydro-2-methyl-8alpha-ergolinyl)-formamide, yield 54%
- from 9,10-didehydro-2,3beta-dihydro-2-ethyl-6-n-propyl- 8alpha-ergolinylamine the N-(9,10-didehydro-2,3beta-dihydro- 2-ethyl-6-n-propyl-8alpha-ergolinyl)-formamide, yield 71%

EXAMPLE 5

Analogously to example 3, there are obtained:
- from N-(9,10-didehydro-2,3beta-dihydro-2-methyl-6-n-propyl-8alpha-ergolinyl)-formamide by oxidation with tert-butyl hypochlorite the N-(9,10-didehydro-2-methyl-6-n-propyl-8-alpha-ergolinyl)-formamide, yield 66%
- from N-(6-allyl-9,10-didehydro-2,3beta-dihydro-2-methyl- 8-alpha-ergolinyl)-formamide the N-(6-allyl-9, 10-didehydro- 2-methyl-8alpha-ergolinyl)-formamide yield 48%
- from N-(9,10-didehydro-2,beta-dihydro-2-ethyl-6-n-propyl8alpha-ergolinyl)-formamide the N-(9,10-didehydro-2-ethyl-6-n-propyl- 8alpha-ergolinyl)-formamide, yield 63%.

EXAMPLE 6

N-(2-methyl-6-n-propyl-8alpha-ergolinyl)-methoxyacetamide 849 mg of 2-methyl-6-n-propyl-8-alpha-ergolinylamine (3 mmol) is dissolved in 20 ml of pyridine and stirred with 2.28 ml of methoxy acetyl chloride (30 mmol) for 30 minutes at room temperature. Then it is poured onto ice, stirred for 15 minutes, make alkaline with ammonia and extracted with dichloromethane. The organic phases are dried and concentrated by evaporation, the residue is chromatographed on silica gel with ethyl acetate/methanol and crystallized from ethyl acetate. Yield 429 mg (40% of theory), $[\alpha]_D=+24°$ (0.5% in chloroform).

EXAMPLE 7

By acylation with the corresponding carboxylic acid chlorides or art hydrides, analogously to example 6, the following amides are obtained:
- N-(2,3-dihydro-2-methyl-6-n-propyl-8alpha-ergolinyl)-methoxyacetamide, yield 63%
- N-(2-methyl-6-n-propyl-8alpha-ergolinyl)-acetoxyacetamide, yield 19%, $[\alpha]_D=+27°$ (0.5% in chloroform).
- N-(9,10-didehydro-2,3-dihydro-2methyl-6-n-propyl-8alpha-ergolinyl)-acetoxyacetamide, yield 41%.

EXAMPLE 8

Analogously to example 3, N-(9,10-didehydro-2-methyl-6-n-propyl- 8alpha-ergolinyl)-acetoxyacetamide is obtained from N-(9,10-didehydro-2,3-dihydro-2-methyl-6-n-propyl-8alpha-ergolinyl)-acetoxyacetamide by oxidation with tert-butyl hypochlorite, yield 63%.

EXAMPLE 9

N-(2-methyl-6-n-propyl-8alpha-ergolinyl)-2-hydroxyacetamide 530 mg of N-(2-methyl-6-n-propyl-8alpha-ergolinyl)-acetoxyacetamide (1.38 mmol) is dissolved in 20 ml of methanol and 0.5 ml of KOH and stirred for 15 minutes at room temperature. Then it is mixed with ice and shaken out with dichloromethane. The organic phases are dried, concentrated by evaporation and crystallized from diisopropyl ether/hexane, yield 321 mg (63% of theory). $[\alpha]_D+20°$ (0.5% in chloroform).

Analogously, the hydrolysis results in the following 2-hydroxyacetmide:
- N-(9,10-didehydro-2-methyl-6-n-propyl-8alpha-erg olinyl)-2-hydroxyacetamide

EXAMPLE 10

Analogously to example 6, the following amides are obtained by acylation with other carboxylic acid chlorides:
- N-(2-methyl-6-n-propyl-8alpha-ergolinyl)-2-methyl-propionamide, yield 21%, $[\alpha]_D=+24°$ (0.5% in chloroform)
- N-(2-ethyl-6-n-propyl-8alpha-ergolinyl)-2-methyl-propionamide, yield 35%

N-(9,10-didehydro-2,3beta-dihydro-2-methyl-6-n-propyl-8alpha-ergolinyl)-2-methyl-propionamide, yield 42%

N-(2-methyl-6-n-propyl-8alpha-ergolinyl)-2-methyl-2-ethyl-butylamide, yield 31%, N-(2-methyl-6-n-propyl-8alpha-ergolinyl)-trifluroacetamide, yield 52%, N-(2-methyl-6-n-propyl-8alpha-ergolinyl)-methane sulfonic acid amide, yield 47%,

EXAMPLE 11

Analogously to example 3, N-(9,10-didehydro-2-methyl-6-n-propyl-8alpha-ergolinyl)-2-methyl-propionamide is obtained from N-(9,10-didehydro-2,3beta-dihydro-2-methyl-6-n-propyl-8alpha-ergolinyl)- 2-methyl-propionamide by oxidation with tert-butyl hypochlorite, yield 72%.

EXAMPLE 12

1-Ethyl-3(2-methyl-6-n-propyl-8alpha-ergolinyl)-urea 880 mg of 2-methyl-6-n-propyl-8alpha-ergolinylamide (3.1 mmol) is dissolved in 100 ml of dichloromethane, 1.0 g of 1,1-carbonyldiimidazole (6.2 mmol) is added under ice cooling and stirred for 2 hours at room temperature. Then 5 ml of a solution of ethylamine in dichloromethane (about 30 mmol) is added, it is stirred for 2 more hours at room temperature, is mixed with ice and ammonia solution and shaken out with dichloromethane. The organic phases are dried and concentrated by evaporation, the residue is chromatographed on silica gel with dichloromethane/methanol, yield 73%

Analogously other ureas are prepared with 1,1'-carbonyldiimidazole and thioureas with different primary and secondary amines with 1,1'-thiocarbonyldiimidazole.

3-(9,10-didehydro-2,3beta-dihydro-2-methyl-6-n-propyl-8alpha-ergolinyl)-1-ethylurea, yield 81%

1,1-dimethyl-3-(2-methyl-6-n-propyl-8alpha-ergolinyl)-urea, yield 65%

1,1-dimethyl-3-(2-ethyl-6-n-propyl-8alpha-ergolinyl)-urea, yield 73%

3-(2-methyl-6-propyl-8alpha-ergolinyl)-1-morpholino-urea, yield 67%, $[\alpha]_D=+15°$ (0.5% in chloroform)

1-dimethylaminoethy-1-ethyl-3-(2-methyl-6-n-propyl-8alpha-ergolinyl)-urea, yield 53%

3-(2-methyl-6-n-propyl-8alpha-ergolinyl)-1,1-di-( 2-trifluoroethyl)-urea, yield 45%

O-(3-dimethylaminopropyl)-N-(2-methyl-6-n-propyl-8alpha-ergolinyl)-urethane, yield 37%

3-(9,10-didehydro-2,3-beta-dihydro-2-methyl-6-n-propyl-8alpha-ergolinyl)-1-dimethylaminoethyl-1-ethylurea, yield 22%

1,1-dimethyl-3-(2-methyl-6-n-propyl-8alpha-ergolinyl)-thiourea, yield 58%

1-ethyl-3-(2-methyl-6-n-propyl-8alpha-ergolinyl)-thiourea, yield 73%

1-dimethylaminoethyl-1-ethyl-3-(2-methyl-6-n-propyl-8alpha-ergolinyl)-thiourea, yield 63%

EXAMPLE 13

Analogously to example 3,3-(9,10-didehydro-2-methyl-6-n-propyl- 8alpha-ergolinyl)-1-ethylurea, yield 43%, is obtained from 3-(9,10-didehydro-2,3beta-dihydro-2-methyl-6-n-propyl-8alpha-ergolinyl)- 1-ethylurea by oxidation with tert-butyl hypochlorite, and 3-(9,10-didehydro-2-methyl-6-n-propyl-8alpha-ergolinyl)-1-dimethylaminoethyl-1-ethylurea, yield 66%, is obtained from 3-(9,10-didehydro-2,3beta-dihydro-2-methyl-6-n-propyl,8alpha-ergolinyl)- 1-dimethylaminoethyl-1-ethylurea.

EXAMPLE 14

N-(2-Methyl-6-n-propyl-8alpha-ergolinyl)-2-methyl-thiopropionic acid amide 353 mg of N-(methyl-6-n-propyl-8alpha-ergolinyl)-2-methylpropionamide (1 mmol) is suspended in 20 mnl of toluene, 404 mg of 2,4-bis-(4-dimethoxyphenyl-1,2,3,4-diethiadiphosphetane- 2,4-disulfide (2 mmol) (Lawesson's reagent) is added and heated for 3 hours to 100° C. After cooling, water is added, it is made alkaline with ammonia and shaken out with dichloromethane. The organic phases was dried and concentrated by evaporation, the residue is chromatographed with dichloromethane/methanol on silica gel, and crystallized from ethyl acetate/diisopropyl ether/hexane yield 55%, $[\alpha]_D=+116°$ C. (0.5% in chloroform)

Analogously, the following thioamides are prepared from the amides:

N-(2-methyl-6-n-propyl-8alpha-ergolinyl)-thioformamide, yield 55%, $[\alpha]_D=+123°$ (0.5% in chloroform)

N-(2-methyl-6-n-propyl-8alpha-ergolinyl)-methoxythioacetamide, yield 68%, $[\alpha]_D=+101°$ (0.5% in chloroform)

N-(2-methyl-6-n-propyl-8alpha-ergolinyl)-2-mercaptothioacetamide yield 46%, $[\alpha C]_D=-70°$ (0.2% in chloroform)

N-(9,10-didehydro-2-methyl-6-n-propyl-8alpha-ergolinyl)-2-methyl-thiopropionic acid amide, yield 34%

N-(2-methyl-6-n-propyl-8alpha-ergolinyl)-2-ethyl-2-methyl-thiobutyric acid amide, yield 54%

EXAMPLE 15

1-Methyl-3-(2-methyl-6-n-propyl-8alpha-ergolinyl)-thiourea 283 mg of 2-methyl-6-n-propyl-8alpha-ergolinylamine (1 mmol) is dissolved in 5 ml of dichloromethane and mixed with 150 mg of methylisothiocyanate (2 mmol) in 5 ml of dichloromethane. It is stirred for 2 hours at room temperature, then mixed with water and ammonia and shaken out with dichloromethane. The organic phases are dried and concentrated by evaporation, the residue is chromatographed on silica gel with dichloromethane/methanol and crystallized, yield 67%, Analogously, the 1-methyl-3-(2-methyl-6-n-propyl-8alpha-ergolinyl)-urea is prepared with methylisocyanate, yield 53%.

EXAMPLE 16

N-(2-Methoxymethyl-6-n-propyl-8alpha-ergolinyl)-formamide 1.1 g of 2-morpholinomethyl-6-n-propyl-8alpha-ergolinylamine (3 mmol) is formylated as described in example 4, then mixed, in 50 ml of tetrahydrofuran, with 2 ml of methyl iodide and stirred for 20 hours at room temperature. Then it is cooled in an ice bath and mixed with diisopropyl ether for completion of the crystallization. The crystals are isolated and dissolved in 30 ml of methanol. At the same time, a methylate solution, in which the solution of the quarternary salt is instilled at 0° C., is prepared from 230 mg of sodium (10 mmol) in 20 ml of methanol. After 15 minutes stirring at 0° C. and 30 minutes at room temperature, ice is added and extraction is performed with dichloromethane. The organic phases are dried and concentrated by evaporation, the residue is chromatographed on silica gel with dichloromethane and methanol, yield 470 mg (48% of theory).

EXAMPLE 17

N-(2-Methylthiomethyl-6-n-propyl-8alpha-ergolinyl)-formamide

If sodium methane thiolate is used as nucleophile analogously to example 16, the title compound in 37% yield is obtained in dichloromethane.

EXAMPLE 18

N-(6-n-Propyl-2-vinyl-8alpha-ergolinyl)-formamide 1.1 g of 2-morpholinomethyl-6-n-propyl-8alpha-ergolinylamine (3 mmol) is formylated as described in example 4, then dissolved in 50 ml of tetrahydrofuran and 1 ml of triethylamine, cooled to −40° C. and mixed with a solution of 0.5 ml of tert-butyl hypochlorite in 10 ml of tetrahydrofuran. After 30 minutes stirring, the batch is poured on ice, made alkaline with ammonia and extracted with dichloromethane. The organic phases are dried and concentrated by evaporation. The residue is dissolved in 40 ml of tetrahydrofuran and added to a Wittig reagent, which was prepared from 6 g of methyl triphenylphosphonium bromide and 2 g of potassium tert-butylate in 70 ml of tetrahydrofuran by stirring 15 minutes at −78° C. It is allowed to react for 1 hour at −78° C., then heated slowly to −40° C. and stirred for 2 hours at −40° C. Then it is mixed with hydrochloric acid solution, extracted with ethyl acetate and the organic phases dried and concentrated by evaporation. The residue is chromatographed on silica gel with dichloromethane/methanol and crystallized, yield 35%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of Formula I

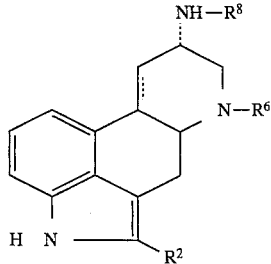

in which

C....C each independently is a single or double bond;

$R^2$ is $C_{1-7}$-alkyl, $C_{2-7}$-alkenyl, $CH_2$—O—$C_{1-4}$-alkyl, $CH_2$—S—$C_{1-4}$-alkyl, or $C_{1-7}$-alkyl substituted with 1–3 of hydroxy, $C_{1-4}$-alkoxy, $C_{2-5}$-acyloxy or C(OR')R"R"', wherein R" and R"' each independently are hydrogen or $C_{1-6}$ alkyl and R' is hydrogen, acetyl or S—$C_{1-4}$-alkyl;

$R^6$ is $C_{3-6}$-alkyl, $C_{3-6}$-alkenyl, or $C_{3-5}$-cycloalkyl—$C_{1-2}$-alkyl;

$R^8$ is —$COCF_3$, —$COR^3$, —CS—O—$(CH_2)_n$—$N(CH_3)_2$ or —CS—S—$C_{1-6}$-alkyl;

$R^3$ is hydrogen, $C_{1-6}$-alkyl, S—$C_{1-6}$-alkyl, —O—$(CH_2)_n$—$N(CH_3)_2$ or $C_{1-6}$-alkyl, singly or doubly substituted with hydroxy, $C_{1-4}$-alkoxy, acetyloxy, or dimethylamino groups; and n is 1, 2, 3, or 4 or a pharmaceutically acceptable acid addition salt thereof, with the proviso that if $R^2$ is methyl, then $R^8$ is not —CO—$C(CH_3)_3$.

2. A compound of the Formula I

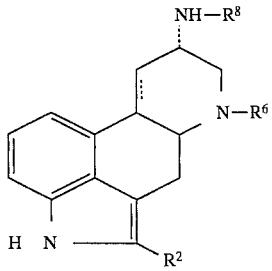

in which

C....C each independently is a single or double bond;

$R^2$ is $C_{1-7}$-alkenyl, $C_{2-7}$-alkenyl, $CH_2$—O—$C_{1-4}$-alkyl, $CH_2$—S—$C_{1-4}$-alkyl, or $C_{1-7}$-alkyl substituted with 1–3 of hydroxy, $C_{1-4}$-alkoxy, $C_{2-5}$-acyloxy or C(OR')R"R"', wherein R" and R"' each independently are hydrogen or $C_{1-6}$-alkyl and R' is hydrogen, acetyl or S—$C_{1-4}$-alkyl;

$R^6$ is $C_{3-6}$-alkyl, $C_{3-6}$-alkenyl or $C_{3-5}$-cycloalkyl-$C_{2-5}$-alkyl;

$R^8$ is —$COCF_3$ or —$COR^3$;

$R^3$ is hydrogen, S–$C_{1-6}$-alkyl, $C_{1-6}$-alkyl or $C_{1-6}$ alkyl, singly or doubly substituted with hydroxy, $C_{1-4}$-alkoxy, acetyloxy, or dimethylamino groups; and n is 1, 2, 3, or 4 or a pharmaceutically acceptable acid addition salt thereof, with the proviso that if $R^2$ is methyl, then $R^3$ is not $C_3$–$C_6$-alkyl.

3. A compound of claim 1, wherein $C_2$....$C_3$ is a saturated bond.

4. A compound of claim 1, wherein $C_2$....$C_3$ is an unsaturated bond.

5. A compound of claim 1, wherein $C_9$....$C_{10}$ is a saturated bond.

6. A compound of claim 1, wherein $C_9$....$C_{10}$ is an unsaturated bond.

7. A compound of claim 1, wherein $R^6$ is alkyl, alkenyl, or cycloalkylalkyl.

8. A compound of claim 1, wherein $R^6$ is $C_{3-4}$-alkyl, $C_{3-4}$-alkenyl, or cycloalkylalkyl of up to 5 total C atoms.

9. A compound of claim 1, wherein $R^2$ is alkyl or alkenyl.

10. A compound of claim 1, wherein $R^2$ is $C_{1-4}$-alkyl or $C_{2-4}$-alkenyl.

11. A compound of claim 1, wherein $R^8$ is —$COR^3$.

12. (Dimethylamino)-(2-methyl-6-n-propyl-8α-ergolinylamino)-sulfone, (9,10-didehydro-2-methyl-6-n-propyl-8alpha-ergolinyl)-dimethylaminosulfone, N-(2-methyl-6-n-propyl-8alpha-ergolinyl)-formamide, N-(9,10-didehydro-2-methyl-6-n-propyl-8alpha-ergolinyl)-formamide,
N-(2-methyl-6-n-propyl-8alpha-ergolinyl)-methoxyacetamide,
N-(2-methyl-6-n-propyl-8alpha-ergolinyl)-acetoxyacetamide,
N-(2-methyl-6-n-propyl-8alpha-ergolinyl)-2-hydroxyacetamide,
N-(2-methyl-6-n-propyl -8alpha-ergolinyl)-2-methyl-propionamide
1-ethyl-3-(2-methyl-6-n-propyl-8alpha-ergolinyl)-urea,
N-(2-methoxymethyl-6-n-propyl-8alpha-ergolinyl-formamide,
N-(6-n-propyl-2-vinyl-8alpha-ergolinyl)-formamide, N-(2-methyl-6 -n-propyl-8α-erolinyl)-trifluoroacetamide, or
N-(2-methyl-6-n-propyl-8α-ergolinyl)-dithiocarbamic acid methyl ester trifluoroacetamide methyl ester, each a compound of claim 1.

13. A compound of the Formula II

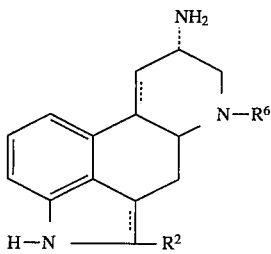

II wherein $R^2$ is substituted or unsubstituted $C_{1-7}$-alkyl, or $C_{1-7}$alkenyl, $CH_2-O-C_{1-4}$ alkyl, or $CH_2-S-C_{1-4}$-alkyl; and $R^6$ is $C_{3-6}$-alkyl, $C_{3-6}$-alkenyl, or $C_{3-5}$-cycloalkyl—$C_{1-2}$-alkyl.

14. A compound of Formula VI

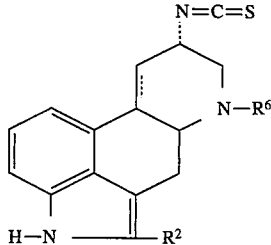

VI wherein $R^2$ is substituted or unsubstituted $C_{1-7}$-alkyl, or $C_{2-7}$-alkenyl, $CH_2-O-C_{1-4}$-alkyl, or $CH_2-S-C_{1-4}$-alkyl; and $R^6$ is $C_{3-6}$-alkyl, $C_{3-6}$-alkenyl, or $C_{3-5}$-cycloalkyl—$C_{1-2}$-alkyl.

15. A composition comprising a compound of claim 1 and a pharmaceutically acceptable carrier.

16. A method of treating Parkinson's Disease comprising administering a compound of claim 1.

17. A compound of claim 1, wherein $R^8$ is —C—S—S—$C_{1-6}$-alkyl, or C—S—O—$(CH_2)_n$ or —$N(CH_3)_2$.

* * * * *